US012691469B2

(12) United States Patent
Liu et al.

(10) Patent No.: US 12,691,469 B2
(45) Date of Patent: Jul. 28, 2026

(54) ULTRASONIC EXTRACTION DEVICE FOR PLANT POLYPHENOLS

(71) Applicant: ZHEJIANG UNIVERSITY, Hangzhou (CN)

(72) Inventors: Donghong Liu, Hangzhou (CN); Wenjun Wang, Hangzhou (CN); Jiaheng Li, Hangzhou (CN); Jianwei Zhou, Hangzhou (CN); Ruiling Lv, Hangzhou (CN); Enbo Xu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 351 days.

(21) Appl. No.: 18/542,624

(22) Filed: Dec. 16, 2023

(65) Prior Publication Data

US 2025/0050379 A1      Feb. 13, 2025

(30) Foreign Application Priority Data

Aug. 10, 2023    (CN) .......................... 202311006478.0

(51) Int. Cl.
| | |
|---|---|
| *B06B 1/06* | (2006.01) |
| *C12N 9/42* | (2006.01) |
| *C12P 7/22* | (2006.01) |

(52) U.S. Cl.
CPC .......... *B06B 1/0644* (2013.01); *C12N 9/2437* (2013.01); *C12P 7/22* (2013.01); *B06B 2201/55* (2013.01); *C12Y 302/01004* (2013.01)

(58) Field of Classification Search
None
See application file for complete search history.

(56) References Cited

FOREIGN PATENT DOCUMENTS

| | | | | |
|---|---|---|---|---|
| CN | 1952046 A | * | 4/2007 | |
| WO | WO-2009071294 A2 | * | 6/2009 | ................ C02F 3/28 |

* cited by examiner

*Primary Examiner* — Krishnan S Menon
(74) *Attorney, Agent, or Firm* — Nolte Lackenbach Siegel

(57) ABSTRACT

An ultrasonic extraction device for plant polyphenols is provided, which includes an ultrasonic processor system, configured for conducting ultrasonic-assisted enzymatic hydrolysis on mixed cellulase solution and plant raw material suspension to extract plant polyphenols; a reactor flow system, including a first reactor flow subsystem, wherein the first reactor flow subsystem is configured for mixing cellulase solution and plant raw material suspension and conveying mixed cellulase solution and plant raw material suspension into the ultrasonic processor system, and the mixed cellulase solution and plant raw material suspension can circulate in the ultrasonic processor system; and a reactor control system, configured for detecting temperature in the ultrasonic processor system and concentration of plant polyphenols in the solution after reaction in the ultrasonic processor system, and controlling working conditions of the ultrasonic processor system and the reactor flow system accordingly.

6 Claims, 1 Drawing Sheet

ULTRASONIC EXTRACTION DEVICE FOR PLANT POLYPHENOLS

CROSS-REFERENCE TO RELATED APPLICATION

This patent application claims the benefit and priority of Chinese Patent Application No. 2023110064780 filed with the China National Intellectual Property Administration on Aug. 10, 2023, the disclosure of which is incorporated by reference herein in its entirety as part of the present application.

FIGURE SELECTED FOR PUBLICATION

FIG. 1.

TECHNICAL FIELD

The present disclosure relates to the technical field of plant polyphenol extraction, and in particular to an ultrasonic extraction device for plant polyphenols.

BACKGROUND

Natural plant polyphenols are usually found in flowers, fruits and peels of plants. There are various types and sources of natural plant polyphenols with the advantages of safety, non-toxic and low cost, and are often used as colorants in industries such as food, cosmetics and textiles. Combined with the positive effects of the natural plant polyphenols in improving biological activity, higher requirements are put forward for the productivity and efficiency of natural plant polyphenol extraction and processing. It is worth noting that the processing by-products of various plants are rich in plant polyphenols, especially for the peel residues of citrus, corn and other fruits and vegetables. However, the peel residues are difficult to extract due to their dense fiber structure, and are often directly discarded, resulting in waste of resources. Enzymatic hydrolysis technology can effectively reduce the mass transfer resistance and increase the diffusion rate of plant polyphenols through enzymatic degradation of cellulose layer outside plant cells, thus improving the extraction rate. However, single enzymatic degradation still has problems such as low efficiency, so it is often assisted by physical techniques such as ultrasonic wave application in the enzymatic hydrolysis process.

Ultrasonic wave is a kind of longitudinal wave with a frequency greater than 20 kHz, which has a significant effect in accelerating enzymatic degradation and promoting the diffusion of components through cavitation when propagating in the medium. The effect of ultrasonic wave on enzymatic degradation reaction can be mainly summarized as its influence on the activity of enzyme, substrate structure and mass transfer process. An enzyme reaction device for extracting natural pigment from roses is disclosed in the patent application CN202122509409.4, which provides a reaction environment for enzymatic hydrolysis extraction of pigment through a reaction tank with stirring and heating functions. A method for extracting red pitaya pigment with assistance of cellulase and ultrasonic wave is disclosed in the patent application CN201910679966.5. The pigment is extracted by cellulase and ultrasonic wave treatment, so as to solve the problems of low pigment dissolution rate and time consumption during extraction and processing. However, in the prior art, there is no continuous device designed for ultrasonic-assisted enzymatic hydrolysis extraction process to maximize the effects of ultrasound and enzyme in the pigment extraction process Therefore, on the basis of a thorough understanding of the ultrasonic-assisted enzymatic hydrolysis extraction process, and combined with real-time monitoring and process control technology, a novel ultrasonic-assisted enzymatic hydrolysis extraction device is proposed, which is important for achieving the automation and intelligence of plant polyphenol extraction process.

SUMMARY

An objective of the present disclosure is to provide an ultrasonic extraction device for plant polyphenols to solve the problems in the prior art. Based on online detection and control technology, a continuous and automatic extraction processing is achieved by means of valve regulation.

To achieve the objective above, the present disclosure provides the following technical solution:

An ultrasonic extraction device for plant polyphenols provided in the present disclosure includes an ultrasonic processor system, the ultrasonic processor system is configured for conducting ultrasonic-assisted enzymatic hydrolysis on mixed cellulase solution and plant raw material suspension to extract plant polyphenols: a reactor flow system, including a first reactor flow subsystem, wherein the first reactor flow subsystem is configured for mixing cellulase solution and plant raw material suspension and conveying mixed cellulase solution and plant raw material suspension into the ultrasonic processor system, and the mixed cellulase solution and plant raw material suspension is capable of circulating in the ultrasonic processor system; and a reactor control system, configured for detecting temperature in the ultrasonic processor system and concentration of plant polyphenols in the solution after reaction in the ultrasonic processor system, and controlling working conditions of the ultrasonic processor system and the reactor flow system accordingly. In the present disclosure, for the problems of difficulty in extracting natural plant polyphenols from plant raw materials, complicated operation steps, lack of product quality control and the like, an ultrasonic-assisted enzymatic hydrolysis technology is used to reduce the mass transfer resistance of plant polyphenols diffusion, and a two-step reaction system of activating cellulase and assisting enzymatic hydrolysis extraction by ultrasonic wave is innovatively proposed, which greatly improves the extraction yield and efficiency of plant polyphenols, and can achieve a continuous and automatic extraction processing by means of valve regulation based on online detection and control technology.

Optionally, the ultrasonic processor system includes multiple ultrasonic processors serially connected in sequence by pipelines. Each ultrasonic processor includes a feed port and a discharge port communicating with an inner chamber of the ultrasonic processor, respectively. In different embodiments, the ultrasonic processors can be specifically named as a first ultrasonic processor, a second ultrasonic processor, a third ultrasonic processor to a N-th ultrasonic processor in sequence according to the number of the ultrasonic processors, and respective feed ports and discharge ports of the ultrasonic processors can be correspondingly named as a first feed port and a first discharge port, a second feed port and a second discharge port to a N-th feed port and a N-th discharge port. The feed port of each ultrasonic processor is connected to the discharge port of an adjacent ultrasonic processor by a pipeline: the feed port of the ultrasonic processor at an outermost end and the discharge port of the ultrasonic processor at another outermost end are connected to the reactor flow system, respectively. An ultrasonic transducer is installed on each ultrasonic processor.

Optionally, the first reactor flow subsystem includes a first liquid pump, a second liquid pump, and a third liquid pump. The reactor control system includes a first gate valve, a second gate valve, a first three-way valve, a second three-way vale, and a PID (Proportional-Integral-Derivative) controller. The first gate valve is arranged on a pipeline communicating with the first liquid pump, the second gate valve is arranged on a pipeline communicating with the second liquid pump, and ends of the first gate valve and the second gate valve are both connected to a first valve port of the first three-way valve by pipelines. A second valve port of the first three-way valve is connected to the feed port of the ultrasonic processor at the outermost end, a third valve port of the first three-way valve is connected to a third valve port of the second three-way valve, a second valve port of the second three-way valve is connected to the discharge port of the ultrasonic processor at another outermost end, and a first valve port of the second three-way valve is externally connected with a product storage device. The first liquid pump is configured for conveying the plant raw material suspension, the second liquid pump is configured for conveying the cellulase solution. The PID controller is configured for controlling on and off of the first liquid pump, the second liquid pump and the third liquid pump, and opening and closing of the first gate valve, the second gate valve, the first three-way valve and the second three-way valve, respectively.

Optionally, an outer wall of each ultrasonic processor is covered with a thermal insulation jacket, which is formed by a nested outer wall space of the ultrasonic processor. The reactor flow system further includes a second reactor flow subsystem, and the second reactor flow subsystem is configured for circulating a heated liquid within the thermal insulation jacket.

Optionally, the second reactor flow subsystem includes a fourth liquid pump. A liquid inlet and a liquid outlet are formed on each thermal insulation jacket. In some embodiments, the number of liquid inlets and liquid outlets is corresponding to that of the ultrasonic processors, and the liquid inlets and the liquid outlets are a first liquid inlet and a first liquid outlet, a second liquid inlet and a second liquid outlet to a N-th liquid inlet and a N-th liquid outlet, respectively. The liquid inlet of each thermal insulation jacket is connected to the liquid outlet of an adjacent thermal insulation jacket by a pipeline, the liquid inlet of the thermal insulation jacket at the outermost end and the liquid outlet of the thermal insulation jacket at another outermost end are connected to the fourth liquid pump by pipelines, respectively. An electric heating wire is arranged on the pipeline communicating with the fourth liquid pump. In particular, each ultrasonic processor is of a tank-shaped nested structure, the feed port and the discharge port on both sides of the ultrasonic processor are used to allow the mixed plant raw material suspension and cellulase solution to flow and make direct contact with the ultrasonic transducer, and the liquid inlet and the liquid outlet on an outer wall layer are used to allow the circulating water to flow, so as to maintain the optimum extraction temperature.

Optionally, the reactor control system further includes a spectral detector. The spectral detector is arranged on a pipeline communicating between the second three-way valve and the discharge port of the ultrasonic processor at the outermost end adjacent to the second three-way valve. The spectral detector is in signal connection with the PID controller.

Optionally, the reactor control system further includes a temperature sensor. The temperature sensor is arranged at a bottom of one of the ultrasonic processors, and is in signal connection with the reactor control system. The spectral detector is configured for detecting content of plant polyphenols in the extracted solution by means of colorimetric principle, and the temperature sensor is configured for detecting extraction temperature in the ultrasonic processor. Result signals of the content of plant polyphenols and the extraction temperature are output to the PID controller for deviation comparison with preset values. After decision-making, the PID controller is configured to control the opening and closing of the corresponding valve and on and off of the corresponding liquid pump to achieve the regulation of the flow state of the mixed solution in the ultrasonic processor, and the extraction temperature is controlled by controlling the electric heating wire and the corresponding liquid pump.

Optionally, the ultrasonic extraction device for plant polyphenols further includes an ultrasonic preprocessor. The ultrasonic preprocessor is arranged on a pipeline between the second liquid pump and the second gate valve. The ultrasonic preprocessor includes a micro-flow pipeline, an object stage, an upper fixing block, a piezoelectric ceramic, and a lower fixing block. The second liquid pump communicates with an end of the micro-flow pipeline, and the second gate valve communicates with another end of the micro-flow pipeline. The micro-flow pipeline is arranged on the object stage, a bottom of the object stage is arranged on the upper fixing block, the lower fixing block is arranged at a bottom of the upper fixing block, and the piezoelectric ceramic is arranged between the upper fixing block and the lower fixing block. The second liquid pump is a micro-flow injection pump for controlling the cellulase solution to enter the micro-flow pipeline by applying pressure slowly, the cellulase solution is subjected to ultrasonication in the micro-flow pipeline to enhance the catalytic activity of enzyme, and then is mixed with a solvent containing plant raw materials to enter the ultrasonic processors for extraction processing.

Optionally, ultrasonic intensity is 25 W/ml, frequency is 22 kHz, pulse duty ratio is 50%, extraction temperature is 50° C., and mass of the added cellulase solution is 1% of mass of the dry plant raw material.

Compared with the prior art, the present disclosure achieves the following beneficial technical effects:

According to an ultrasonic extraction device for plant polyphenols provided in the present disclosure, online monitoring of the extraction processing of plant polyphenols is achieved through a spectral detector and a temperature sensor, and the process is controlled by combining a gate valve and a liquid pump, so as to ensure that the concentration of the extracted product reaches a set threshold and the extraction temperature is maintained in an optimal range. According to the multi-stage ultrasonic processor provided in the present disclosure, the activity of cellulase before enzymatic reaction is significantly increased by means of ultrasonic treatment. Meanwhile, in the process of enzymatic degradation and extraction, the structure of plant raw materials can be destroyed to accelerate the diffusion process of plant polyphenols, thus maximizing the effect of ultrasonic wave in assisting enzymatic hydrolysis extraction and increasing the total output and production efficiency of plant polyphenols. The requirements of continuous processing in enzymatic extraction are satisfied, the effect and extraction yield of ultrasonic wave are further increased, adjustment can be conducted according to different ultrasonic reaction systems, and the characteristics and advantages of automation and intelligence are achieved.

BRIEF DESCRIPTION OF THE DRAWINGS

To describe the technical solutions of the embodiments of the present disclosure or in the prior art more clearly, the following briefly introduces the accompanying drawings required for describing the embodiments. Apparently, the accompanying drawings in the following description show merely some embodiments of the present disclosure, and those of ordinary skill in the art may still obtain other drawings from these accompanying drawings without creative efforts.

Figure 1:
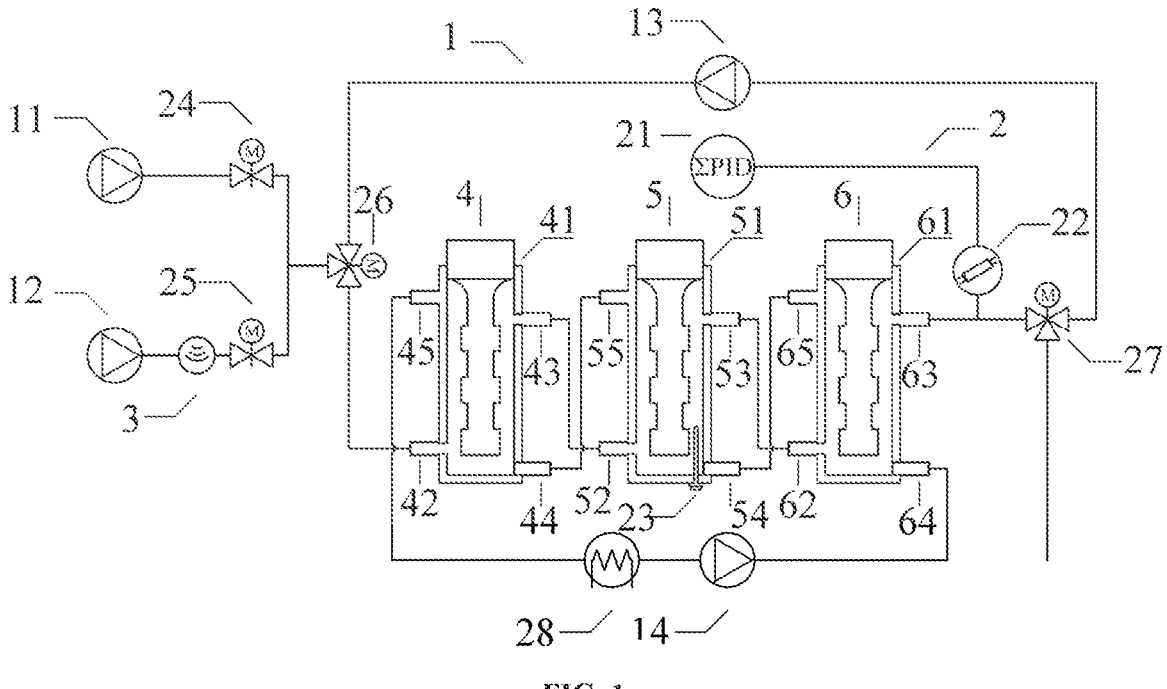
FIG. 1 is a structural schematic diagram of an ultrasonic extraction device for plant polyphenols according to an embodiment of the present disclosure.

In the drawings: 1—reactor flow system; 11—first liquid pump; 12—second liquid pump; 13—third liquid pump; 14—fourth liquid pump; 2—reactor control system; 21—PID controller; 22—spectral detector; 23—temperature sensor; 24—first gate valve; 25—second gate valve; 26—first three-way valve; 27—second three-way valve; 28—electric heating wire; 3—ultrasonic preprocessor; 31—micro-flow pipeline; 32—object stage; 33—upper fixing block; 34—piezoelectric ceramic; 35—lower fixing block; 4—first ultrasonic processor; 41—first ultrasonic transducer; 42—first feed port; 43—first discharge port; 44—first liquid inlet; 45—first liquid outlet; 5—second ultrasonic processor; 51—second ultrasonic transducer; 52—second feed port; 53—second discharge port; 54—second liquid inlet; 55—second liquid outlet; 6—third ultrasonic processor; 61—third ultrasonic transducer; 62—third feed port; 63—third discharge port; 64—third liquid inlet; 65—third liquid outlet.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

An objective of the present disclosure is to provide an ultrasonic extraction device for plant polyphenols to solve the problems in the prior art. Based on the online detection and control technology, a continuous and automatic extraction processing is achieved by means of valve regulation.

In order to make the objectives, technical solutions and advantages of the present disclosure more clearly, the present disclosure is further described in detail below with reference to the embodiments.

Embodiment 1

As shown in FIG. 1, a device for extracting plant polyphenols by ultrasonic-assisted enzymatic hydrolysis based on the control of valve array according to an embodiment is provided, which includes a reactor flow system 1, a reactor control system 2, an ultrasonic preprocessor 3, and an ultrasonic processor system. The ultrasonic processor system includes multiple ultrasonic processors serially connected in sequence by pipelines. In this embodiment, three ultrasonic processors is used as an example for description, that is, the ultrasonic processor system in the embodiment includes a first ultrasonic processor 4, a second ultrasonic processor 5 and a third ultrasonic processor 6 which have the same structure and are connected in series.

The reactor flow system 1 includes a first liquid pump 11, a second liquid pump 12, a third liquid pump 13, and a fourth liquid pump 14. The reactor control system 2 includes a PID controller 21, a spectral detector 22, a temperature sensor 23, a first gate valve 24, a second gate valve 25, a first three-way valve 26, a second three-way valve 27, and an electric heating wire 28. Unless otherwise specified, all components for conveying plant raw material suspension are connected by pipelines, and the valves and liquid pumps are adjusted by the PID controller 21 according to detection results in the process. The first liquid pump 11 is responsible for conveying the plant raw material suspension through the first gate valve 24, the second liquid pump 12 is configured for conveying cellulose liquid through the ultrasonic preprocessor 3 and the second gate valve 25, where the proportion of cellulase and plant raw materials is controlled at 1%, and solid-liquid ratio is 1:30. After being mixed, mixture of plant raw material suspension and cellulase solution flow through the first ultrasonic processor 4, the second ultrasonic processor 5 and the third ultrasonic processor 6 along a left-down flow direction of the first three-way valve 26, and a result signal obtained after colorimetric detection by the spectral detector 22 is determined by the PID controller 21. If a detection value is higher than a set value, the mixture of plant raw material suspension and cellulase solution flows out along a left-down flow direction of the second three-way valve 27, thus obtaining plant raw material and plant polyphenol solution after extraction. If the detection value is lower than a set range, the third liquid pump 13 is turned on the mixture re-enters the extraction system along a left-right flow direction of the second three-way valve 27. Meanwhile, the first liquid pump 11 and the second liquid pump 12 are turned off, and the first gate valve 24 and the second gate valve 25 are closed, and thus the mixture enters the first ultrasonic processor 4 along an up-down flow direction of the first three-way valve 26. The ultrasonic-assisted enzymatic hydrolysis extraction process is repeated until the result measured by the spectral detector 22 reaches a set target extraction concentration.

Figure 2:
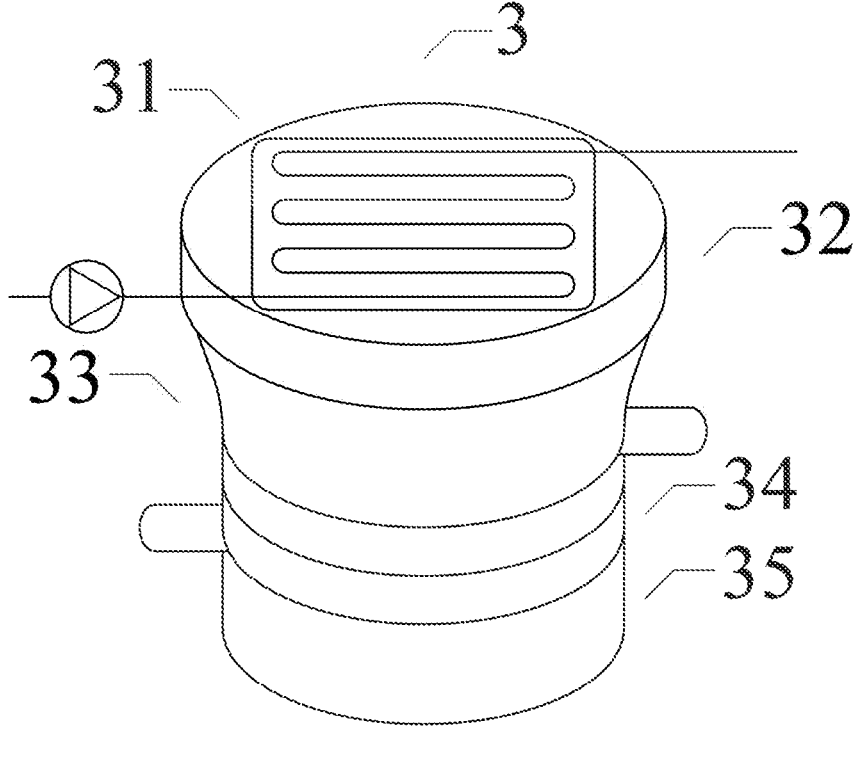
FIG. 2 is a structural schematic diagram of an ultrasonic preprocessor shown in FIG. 1.

As shown in FIG. 2, the ultrasonic preprocessor 3 includes a micro-flow pipeline 31, an object stage 32, an upper fixing block 33, a piezoelectric ceramic 34, and a lower fixing block 35. The micro-flow pipeline 31 is arranged on the object stage 32. The cellulase solution is slowly conveyed into the micro-flow pipeline 31 by the second liquid pump 12, a vibration signal produced by the piezoelectric ceramic 34 is transmitted to the micro-flow pipeline 31 via the upper fixing block 33 and the object stage 32, and the cellulase solution therein is subjected to ultrasonic treatment and then flows out along the pipeline to enter the second gate valve 25.

The first ultrasonic processor 4, the second ultrasonic processor 5 and the third ultrasonic processor 6 have the same function and structure, but the difference is that the temperature sensor 23 is installed at a bottom of the second ultrasonic processor 5 to detect system temperature in the extraction process and feed the system temperature back to the PID controller 21. The system temperature is compared with a set extraction temperature range (50+/−5° C.), so as to adjust the electric heating wire 28. As shown in FIG. 1, taking the first ultrasonic processor 4 as an example, the ultrasonic parameters used in the embodiment are that intensity is 25 W/ml, frequency is 22 kHz, and pulse duty ratio is 50%. The first ultrasonic processor includes a first ultrasonic transducer 41, a first feed port 42, a first discharge port 43, a first liquid inlet 44, and a first liquid outlet 45. During the operation of the ultrasonic extraction device, the proportionally mixed plant raw material and cellulase solution enter a chamber of the first ultrasonic processor 4 from the first feed port 42 at a bottom of the first ultrasonic processor, mechanical vibration produced by the first ultrasonic transducer 41 is directly transmitted to a sample to be treated, and then the sample enters a second feed port 52 of the second ultrasonic processor 5 from the first discharge port 43 at a top of the first ultrasonic processor. A mechanical vibration produced by a second ultrasonic transducer 51 is directly transmitted to the sample to be treated, then the sample enters a third feed port 62 of the third ultrasonic processor 6 from a second discharge port 53 at a top of the second ultrasonic processor. A mechanical vibration produced by a third ultrasonic transducer 61 is directly transmitted to the sample to be treated, and so on until the sample flows out from a third discharge port 63 of the third ultrasonic processor 6 to complete a single extraction. A nested outer wall space outside the ultrasonic processor forms a thermal insulation jacket. Circulating water is heated by the electric heating wire 28 and pumped by the fourth liquid pump 14 into a third liquid inlet 64 at a bottom of the third ultrasonic processor 6. After flowing through the nested outer wall space, the circulating water flows out from a third liquid outlet 65 at a top of the third ultrasonic processor to enter a second liquid inlet 54 at the bottom of the second ultrasonic processor 5. After flowing through the nested outer wall space, the circulating water flows out from a second liquid outlet 55 at the top of the second ultrasonic processor to enter the first liquid inlet 44 at the bottom of the first ultrasonic processor 4, and so on until the circulating water flows out from the first discharge port 45 at the top of the first ultrasonic processor 4 to complete a single water bath circulation.

In the description of the present disclosure, it should be noted that the orientation or positional relationship indicated by terms "center", "top", "bottom", "left", "right", "vertical", "horizontal", "inside" and "outside" is based on the orientation or positional relationship shown in the drawings only for convenience of description of the present disclosure and simplification of description rather than indicating or implying that the device or element referred to must have a particular orientation, be constructed and operated in a particular orientation, and thus are not to be construed as limiting the present disclosure. Furthermore, the terms "first" and "second" are used for descriptive purposes only and are not to be construed as indicating or implying relative importance.

Specific examples are used herein for illustration of the principles and implementation methods of the present disclosure. The description of the embodiments is merely used to help illustrate the method and its core principles of the present disclosure. In addition, a person of ordinary skill in the art can make various modifications in terms of specific embodiments and scope of application in accordance with the teachings of the present disclosure. In conclusion, the content of this specification shall not be construed as a limitation to the present disclosure.

What is claimed is:

1. An ultrasonic extraction device for plant polyphenols, comprising an ultrasonic processor system, wherein the ultrasonic processor system comprises multiple ultrasonic processors, and the ultrasonic processor system is configured for conducting ultrasonic-assisted enzymatic hydrolysis on mixed cellulase solution and plant raw material suspension to extract plant polyphenols;

a reactor flow system, comprising a first reactor flow subsystem, wherein the first reactor flow subsystem comprises a first liquid pump, a second liquid pump, a third liquid pump, and a fourth liquid pump and the first reactor flow subsystem is configured for mixing cellulase solution and plant raw material suspension and conveying mixed cellulase solution and plant raw material suspension into the ultrasonic processor system, and the mixed cellulase solution and plant raw material suspension is capable of circulating in the ultrasonic processor system;

a reactor control system comprises a PID controller, a spectral detector, a temperature sensor, a first gate valve, a second gate valve, a first three-way valve, a second three-way valve, and an electric heating wire, and the reactor control system is configured for detecting temperature in the ultrasonic processor system and concentration of plant polyphenols in the solution after reaction in the ultrasonic processor system, and controlling working conditions of the ultrasonic processor system and the reactor flow system accordingly;

wherein the ultrasonic processor system comprises a plurality of ultrasonic processors serially connected in sequence by pipelines, each ultrasonic processor comprises a feed port and a discharge port communicating with an inner chamber of the ultrasonic processor, respectively; the feed port of each ultrasonic processor is connected to the discharge port of an adjacent ultrasonic processor by a pipeline; the feed port of the ultrasonic processor at an outermost end and the discharge port of the ultrasonic processor at another outermost end are both connected to the reactor flow system; and an ultrasonic transducer is installed on each ultrasonic processor; and wherein the first reactor flow subsystem comprises a first liquid pump, a second liquid pump, and a third liquid pump; the reactor control system comprises a first gate valve, a second gate valve, a first three-way valve, a second three-way vale, and a PID (Proportional-Integral-Derivative) controller; the first gate valve is arranged on a pipeline communicating with the first liquid pump, the second gate valve is arranged on a pipeline communicating with the second liquid pump, ends of the first gate valve and the second gate valve are both connected to a first valve port of the first three-way valve by pipelines, a second valve port of the first three-way valve is connected to the feed port of the ultrasonic processor at the outermost end, a third valve port of the first three-way valve is connected to a third valve port of the second three-way valve, a second valve port of the second three-way valve is connected to the discharge port of the ultrasonic processor at another outermost end, and a first valve port of the second three-way valve is externally connected with a product storage device; the first liquid pump is configured for conveying the plant raw material suspension, the second liquid pump is configured for conveying the cellulase solution; and the PID controller is configured for controlling on and off of the first liquid pump, the second liquid pump and the third liquid pump, and opening and closing of the first gate valve, the second gate valve, the first three-way valve and the second three-way valve, respectively.

2. The ultrasonic extraction device for plant polyphenols according to claim 1, wherein an outer wall of each ultrasonic processor is covered with a thermal insulation jacket; the reactor flow system further comprises a second reactor flow subsystem, and the second reactor flow subsystem is configured for circulating a heated liquid within the thermal insulation jacket.

3. The ultrasonic extraction device for plant polyphenols according to claim 2, wherein the second reactor flow subsystem comprises a fourth liquid pump, a liquid inlet and a liquid outlet are formed on each thermal insulation jacket; the liquid inlet of each thermal insulation jacket is connected to the liquid outlet of an adjacent thermal insulation jacket by a pipeline, the liquid inlet of the thermal insulation jacket at an outermost end and the liquid outlet of the thermal insulation jacket at another outermost end are connected to the fourth liquid pump by pipelines, respectively; and an electric heating wire is arranged on a pipeline communicating with the fourth liquid pump.

4. The ultrasonic extraction device for plant polyphenols according to claim 1, wherein the reactor control system further comprises a spectral detector; the spectral detector is arranged on a pipeline communicating between the second three-way valve and the discharge port of the ultrasonic processor at the outermost end adjacent to the second three-way valve; and the spectral detector is in signal connection with the PID controller.

5. The ultrasonic extraction device for plant polyphenols according to claim 3, wherein the reactor control system further comprises a temperature sensor, the temperature sensor is arranged at a bottom of one of the ultrasonic processors, and the temperature sensor is in signal connection with the reactor control system.

6. The ultrasonic extraction device for plant polyphenols according to claim 1, further comprising an ultrasonic preprocessor, wherein the ultrasonic preprocessor is arranged on a pipeline between the second liquid pump and the second gate valve; the ultrasonic preprocessor comprises a micro-flow pipeline, an object stage, an upper fixing block, a piezoelectric ceramic, and a lower fixing block; the second liquid pump communicates with an end of the micro-flow pipeline, the second gate valve communicates with another end of the micro-flow pipeline, the micro-flow pipeline is arrange on the object stage, a bottom of the object stage is arranged on the upper fixing block, the lower fixing block is arranged at a bottom of the upper fixing block, and the piezoelectric ceramic is arranged between the upper fixing block and the lower fixing block.

* * * * *